US007383081B2

(12) United States Patent
Butt et al.

(10) Patent No.: US 7,383,081 B2
(45) Date of Patent: Jun. 3, 2008

(54) TRAINING DEVICE AND METHOD

(75) Inventors: Phillip Butt, Helsingfors (FI); Mikko Ahlstrom, Helsinki (FI); Kimmo Pernu, Espoo (FI)

(73) Assignee: Suunto Oy, Vantaa (FI)

( * ) Notice: Subject to any disclaimer, the term of this patent is extended or adjusted under 35 U.S.C. 154(b) by 70 days.

(21) Appl. No.: 11/181,836

(22) Filed: Jul. 15, 2005

(65) Prior Publication Data

US 2007/0016091 A1 Jan. 18, 2007

(51) Int. Cl.
*A61B 5/044* (2006.01)

(52) U.S. Cl. ........................ 600/523; 600/519; 600/522

(58) Field of Classification Search ................ 600/481, 600/508, 509, 519, 520, 522, 523, 525; 482/3; 368/277, 278, 281
See application file for complete search history.

(56) References Cited

U.S. PATENT DOCUMENTS

| | | | | |
|---|---|---|---|---|
| 5,769,755 | A * | 6/1998 | Henry et al. | 482/8 |
| 5,876,346 | A | 3/1999 | Corso | |
| 6,042,549 | A * | 3/2000 | Amano et al. | 600/500 |
| 2002/0052556 | A1* | 5/2002 | Nissila | 600/509 |
| 2004/0162188 | A1* | 8/2004 | Watterson et al. | 482/8 |
| 2004/0233788 | A1* | 11/2004 | Plancon et al. | 368/11 |

FOREIGN PATENT DOCUMENTS

| | | | |
|---|---|---|---|
| EP | 0 556 702 | A2 | 8/1993 |
| EP | 0 761 163 | A2 | 3/1997 |
| EP | 0 842 635 | A1 | 5/1998 |
| EP | 1195134 | | 4/2002 |
| EP | 1 245 184 | A2 | 10/2002 |
| EP | 1498790 | | 1/2005 |
| GB | 2 368 124 | A | 4/2002 |
| WO | WO-90/00366 | A1 | 1/1990 |

* cited by examiner

*Primary Examiner*—Carl Layno
*Assistant Examiner*—Eugene T Wu
(74) *Attorney, Agent, or Firm*—Birch, Stewart, Kolasch & Birch, LLP

(57) ABSTRACT

A wristop heart rate monitor comprising a dial, which comprises a current heart rate indicator, which is responsive to a heart rate signal measured from a user of the wristop heart rate monitor and functionally connected to a heart rate scale, and a reference indicator defining a visually identifiable reference heart rate range. At least one of the indicators is rotatably adjustable relative to the dial, and the heart rate scale and the reference heart rate range are adjustable relative to each other. A method is also described for monitoring the heart rate of a sportsman. The wristop heart rate monitor provides a quickly perceivable and adjustable heart rate monitor structure.

15 Claims, 3 Drawing Sheets

TRAINING DEVICE AND METHOD

BACKGROUND OF THE INVENTION

1. Field of the Invention

The invention relates to a performance-monitoring device used in sports. In particular, the invention concerns a wristop device, which can be used for monitoring the intensity of training. Such a device monitors the physiological state of a sportsman and provides training-related data to the sportsman. The invention also concerns a method of carrying out exercise monitoring.

2. Description of Related Art

EP 1245184 discloses a heart rate monitor having a digital display, which comprises panels for showing a lower and higher limit of the heart rate in numbers. A highlighted section of a slide bar is moved between the higher and lower limit to show the current heart rate of the user of the device. The heart rate is also shown in number format in a corner of the display. The device is restricted to showing in an illustrative way only the heart rates between the lower and upper limits. If no section of the slide bar is highlighted, the user has to refer to the number representation of the heart rate. If the linear scale of the slide bar is extended, the resolution degrades to an unusable level due to a limited resolution and size of digital displays.

U.S. Pat. No. 5,876,346 discloses an artery locating device, which has a function of showing heart rate in a linear graphical slide bar.

In EP 0761163, and EP 0842 635 another display method for a heart rate monitor is disclosed. The display has a graphical heart rate bar and a numerical representation of the heart rate.

WO 90/00366 discloses a numerical display having a lower limit of heart rate, a higher limit of heart rate and the actual heart rate shown in numbers.

In many prior art devices, setting of the lower and higher limits for heart rate is very difficult to carry out. In order to be able to set the limits, the user often has to navigate to a correct menu of the device and to tap the setting in by using "increase/decrease value" buttons of the device. The procedure is therefore often left undone in the beginning of an exercise, whereby the useful heart rate limiting function of the device remains unused.

In addition, the prior art solutions related to heart rate monitor displays are such that it is difficult for the user to quickly see the present heart rate and the heart rate limits. When jogging, for example, the device unavoidably shakes, whereby perceiving of the heart rate with respect to the limits takes a long while.

SUMMARY OF THE INVENTION

It is an aim of the invention to provide a novel device structure and method that enable simpler use of a heart rate monitor.

It is also an aim of the invention to provide a device, that is easily configurable to assist follow-through of a particular exercise in a physiologically preferable manner or to correspond to the individual physical condition of a sportsman.

It is also an aim of the invention to provide a novel method for carrying out monitoring of training.

The invention is based on the idea of using an analogue-type (circumferential movement-exhibiting) wristop environment for implementing a technical structure, which takes advantage of a novel combination of visually identifiable current heart rate reference indicators and a reference heart rate range defined by the reference indicators, whereby relative adjustment of the scale of the current heart rate and the reference heart rate range is allowed.

The heart rate monitor according to the invention comprises a dial having a current heart rate indicator and a reference indicator. The current heart rate indicator is responsive to a heart rate signal measured from the user of the device (or from a person wearing its associated sensor device, such as a transmitter belt). The indicator is functionally connected to a heart rate scale. The reference indicator exhibits a visually identifiable reference heart rate range. The scale of the heart rate and the reference heart rate range are adjustable relative to each other.

The method according to the invention comprises monitoring the heart rate of a person by visually indicating current heart rate of the person responsively to a heart rate signal measured from the person, and by visually indicating a reference heart rate range. Visual indication of the current heart rate is regulated by a heart rate scale, which is relatively adjustable with the reference heart rate range.

By a "functional connection" between the current heart rate indicator and the heart rate scale, we mean that the physical positioning of the indicator is bound to an abstract scale, which is stored and possibly adjusted by the hardware or software of the device. That is, a conversion between the actual heart rate and the desired position of the heart rate indicator is needed. The scaling can be totally hidden from the user or shown in the dial.

The positioning areas of the indicators can be arranged on the dial on separate or overlapping zones, preferably of fully or partly elliptical, typically of circular shape. The indicators may comprise traditional hands (pointers), Bezel-mounted members or digital segments, such as LCD or TFT displays. The reference range indicator can also be a printed or rotatable arc, disc or sector on the dial. Movement of the reference indicator is not obligatory. Depending on the embodiment, adjustment (fitting) of the heart rate scale and the reference range can be done either manually or automatically. That is, in the manual mode of operation, the user can, for example, set the reference range by manually rotating the reference indicator (or its sub-elements) on the dial, whereby the range is adjusted with reference to the heart rate scale. In an automated mode of operation the heart rate scale, and thus the behaviour of the current heart rate indicator with respect to the dial, is changed depending on, for example, data collected during previous exercises. Alternatively, adjustment of the reference indicator can be automated.

More specifically, the monitor is characterized by what is stated in claim 5.

The method is characterized in claim 1.

Considerable advantages are obtained by means of the invention. In particular, the need of linking individual heart rate limits to an absolute heart rate scale each time the limits are set is made redundant. That is, if the scale of the heart rate is kept constant, the device does need to know the reference range set by the user. On the other hand, if the scale of the heart rate is adjusted, the user does not need to know the heart rate values of the reference range. This is made possible by a novel positioning and functioning of the heart rate and reference indicators. Thus, the current heart rate indicator and the reference range indicator can function totally independently, which is not possible in the prior art devices, as the current heart rate is always presented relative to the preset limits.

From an average user's point of view, no important functions needed in training are lost. On the contrary, the user may concentrate on doing the exercise on the right heart rate area, listen more to his body and give less or no weight to the absolute heart rate values. In addition, also the time used when programming the heart rate monitor before the exercise can be shortened.

Thus, the described structure allows simple and illustrative usage of the device. From the relative position of the indicators, the user of the device can read the heart rate data related to the ongoing exercise more clearly and in less time. The circumference of a round dial is over three times larger than its diameter. This makes it possible to use a threefold extended heart rate scale compared to prior devices. Thus, the dial area of the device is being used in an efficient manner enabling extending the usable scale of the heart rate indicator and still providing the data on the desired heart rate level.

For most users, the most important aspects in utilizing a heart rate monitor are its easy setting up and good readability. However, the implementation and combining of these aspects has proven difficult. We have found, that a modified analogue watch-type (though not necessarily analogue) implementation of the heart rate and/or heart rate limit data is more graphic and more quickly perceivable in sports. In addition, it provides easily adoptable setting up of heart rate limits or training ranges.

By a rotatable or coaxial arrangements, we mean such solutions, which enable movement of the indicators of heart rate and of the reference range essentially around the dial area of the device. The shapes or the radiuses of movement of the indicators can be any. The indicators can be implemented, for example, by using digital displays or analogue pointers, or a mixture of them. Thus, the term "rotatable" includes also such embodiments, where the indicator is extendable along a curved track. The rotational movement can be arranged to take place, for example, along a full or partial elliptical, preferably circular, track.

By heart rate, we mean the actual pulsing frequency or a measure derived from it (training intensity). Generally, any physiological measure depending on the exertion of the sportsman, and which is measurable by a carry-on device or a set of carry-on devices (such as a chest sensor and a wristop device) can be used.

By a reference range, we mean an arbitrary range of variation of the heart rate. The reference range may thus point to user-defined lower and higher limits of heart rate, between which he or she aims to keep his or her heart rate during an exercise. Alternatively, the reference range may point to a broader heart rate range comprising, for example, visually distinguishable ranges for rest, aerobic training, anaerobic training and maximal output training. The range may be movable or adjustable relative to the dial or statically anchored to the dial.

When referring to the current heart rate or reference indicators, the terms "digital" and "analogue" are generally used to clarify the visual realization of the indicators. The term "digital" is to be understood as an implementation utilizing micro-scale movement of particles, such as in LC-displays. The term "analogue" refers to classical hand-type implementations and other solutions taking advantage of rotating or moving macro-scale pointers. However, the visual realization of the indicators does not restrict the possibilities of electrical or mechanical implementations of the product beyond the dial panel.

Next, the embodiments of the invention are described more closely with reference to the attached drawing.

DETAILED DESCRIPTION OF THE INVENTION

Figure 1:
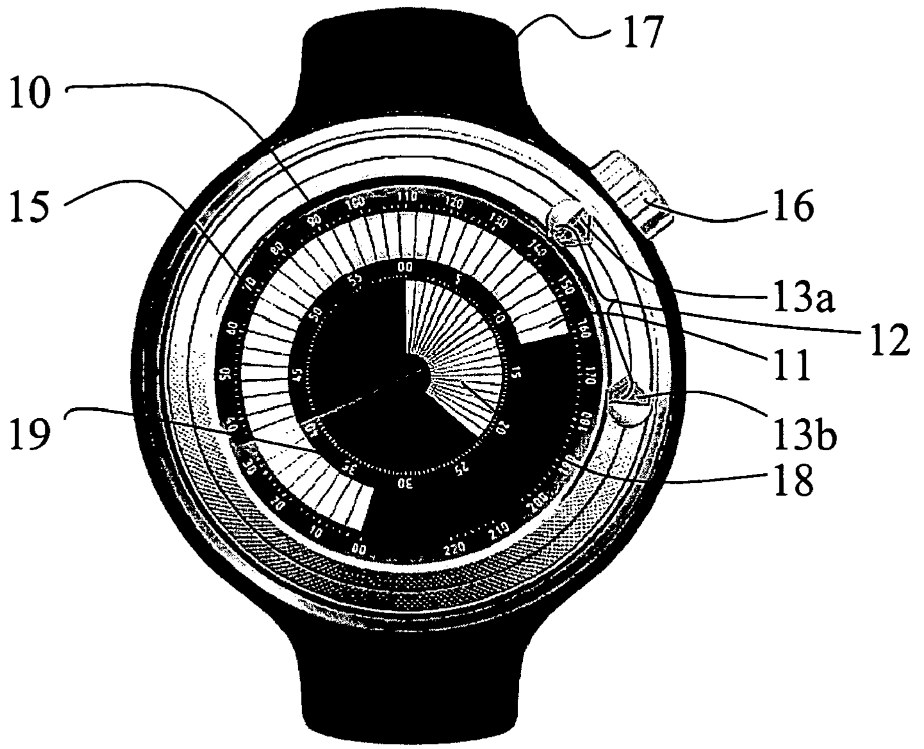
FIG. 1 shows a top view of an embodiment of the invention having a digital current heart rate indicator and a Bezel-mounted reference range indicator.

FIG. 1 shows a first preferred embodiment of a wristop computer according to the invention. The dial of the product is denoted with the reference numeral 10. The current heart rate indicator 11 and the reference indicator are arranged orbicularly in the dial area. The current heart rate indicator 11 is implemented using radially arranged digital display segments, which can be highlighted one after another depending on the current heart rate and the heart rate scale used. The reference indicator comprises a lower level marker 13*a* and a higher level marker 13*b*, which define an intervening reference range 12. In this example, the lower and higher level markers 13*a*, 13*b* comprise Bezel-mounted physical indicators (knobs) which are rotatable along the fringe of the dial. The lower level indicator can be colored green to indicate "go" and the higher level marker can be colored red to indicate "slow down", for example. The lower and higher level markers 13*a*, 13*b* are preferably individually movable but they can also be mechanically connected to each other so that their separation stays constant.

In FIG. 1, also the heart rate scale is shown in the dial as an orbicularly arranged text portion 15 between the indicator zones. An additional digital display portion 18 is arranged in the central part of the dial for displaying, for example, the duration of training, where the duration could be measured in time or calorie consumption, for example. The display portion 18 can also be used to display, for example, current, averaged or cumulative intensity level of the exercise, or a number of laps elapsed. A printed scale 19 can be used in this context. The device preferably also comprises a wristband 17 and a crown 16, which is discussed in more detail later in this document. The knobs can be directly manually movable, mechanically or electronically operable through the crown, or electronically controlled by the wristop computer or a host device the wristop computer is connected to.

Figure 2:
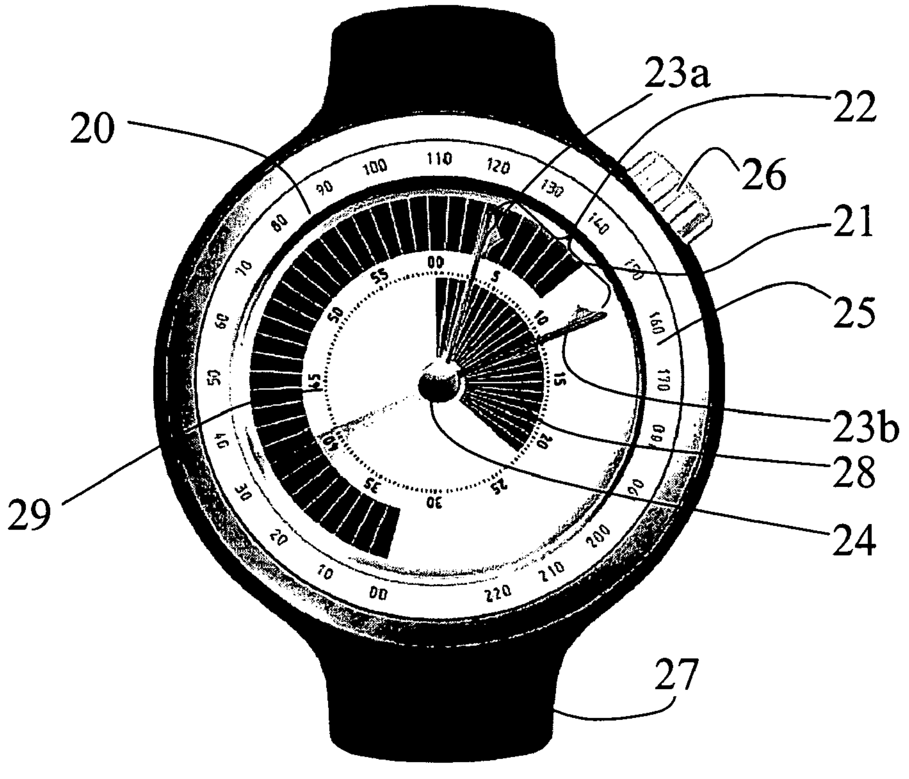
FIG. 2 shows a top view of an embodiment of the invention having a digital current heart rate indicator and a hand-type reference range indicator.

In FIG. 2, a modified embodiment of the device shown in FIG. 1 is shown. In the embodiment, the lower and higher level markers 23*a*, 23*b* of the reference indicator comprise hands rotatably attached to the center of the dial 20. The hands can be operable, for example, through an at least two-function crown 26. Alternatively, the hands may be operated through a vertical crown placed on the rotational axis 24 of the hands.

Figure 3:
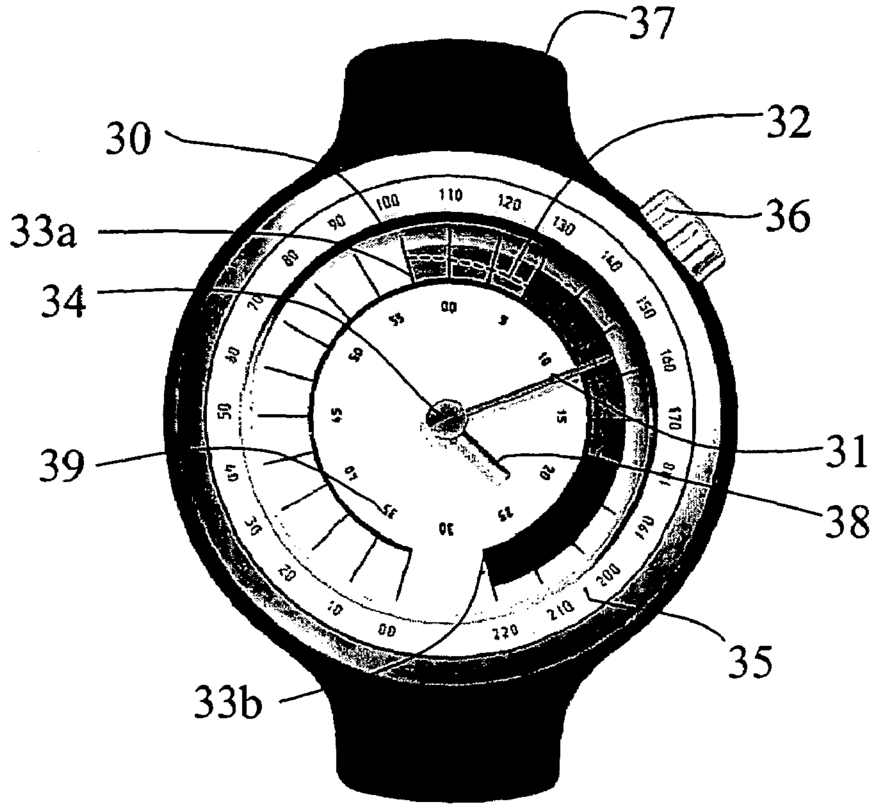
FIG. 3 shows a top view of an embodiment of the invention having a hand-type current heart rate indicator and a rotatable constant-length reference indicator.

FIG. 3 shows an implementation having an analogue hand as the current heart rate indicator 31. In this embodiment, the reference range 32 is indicated with an arched member having a visually identifiable lower level marker 33*a* and a visually identifiable higher level marker 33*b*. The reference range is divided into three portions indicating three different training areas. The arc-shaped member is rotatable as a whole to match the condition and physiological properties of the user of the device. Thus, the separation of the higher and lower level markers 33*a*, 33*b*, along with the intervening training area markers, stays constant, but the location with reference to the dial 30 and to the heart rate scale is changed. The reference indicator can be rotated, for example, by using a crown 36 or 34 fully mechanically and/or by utilizing fully or partly electronic control means.

The reference indicator can also comprise two, three or four independently adjustable members that can be moved relative to the dial and relative to each other manually or automatically. By this fan-like embodiment, a more flexible training zone indicator, where also the sub-ranges can be adjusted independently, can be formed.

The device of FIG. 3 comprises also a second analogue pointer 38 in the form of a second hand, which corresponds to the digital counters 18 and 28 of FIGS. 1 and 2, respectively.

Figure 4:
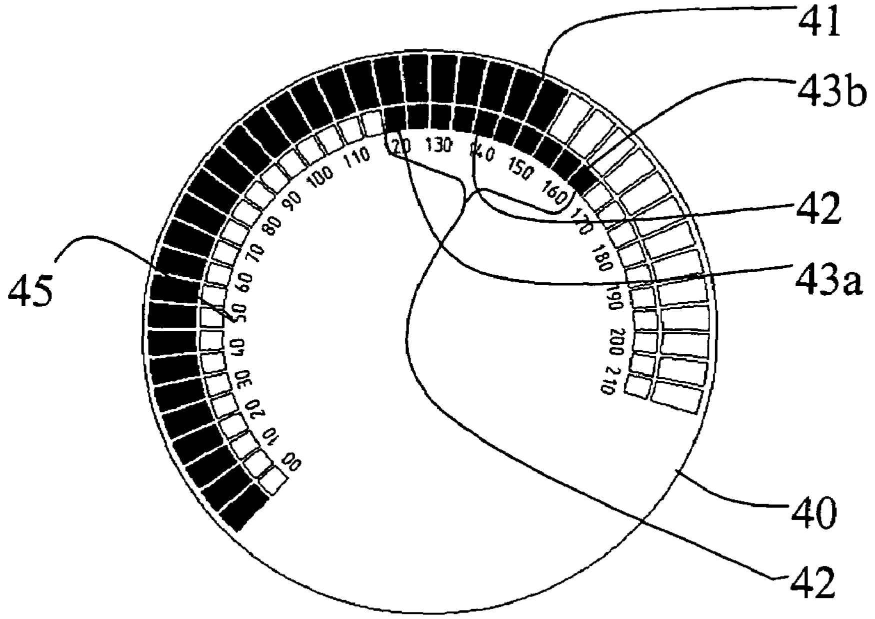
FIG. 4 shows a schematic top view of an embodiment of the invention having a digital current heart rate indicator and a digital reference indicator.

FIG. 4 shows a fully digital equivalent of the embodiments shown in FIGS. 1 and 2. The current 30 heart rate indicator 41 is comprised of radially positioned first digital display segments on an outer zone of the dial 40 and the reference indicator is comprised of radially positioned second digital display segments on an inner zone of the dial 40. The lower level marker 43*a* is indicated by a first highlighted segment and the higher level marker 43*b* is indicated by a second highlighted segment on the opposite ends of the reference range 42.

Figure 5:
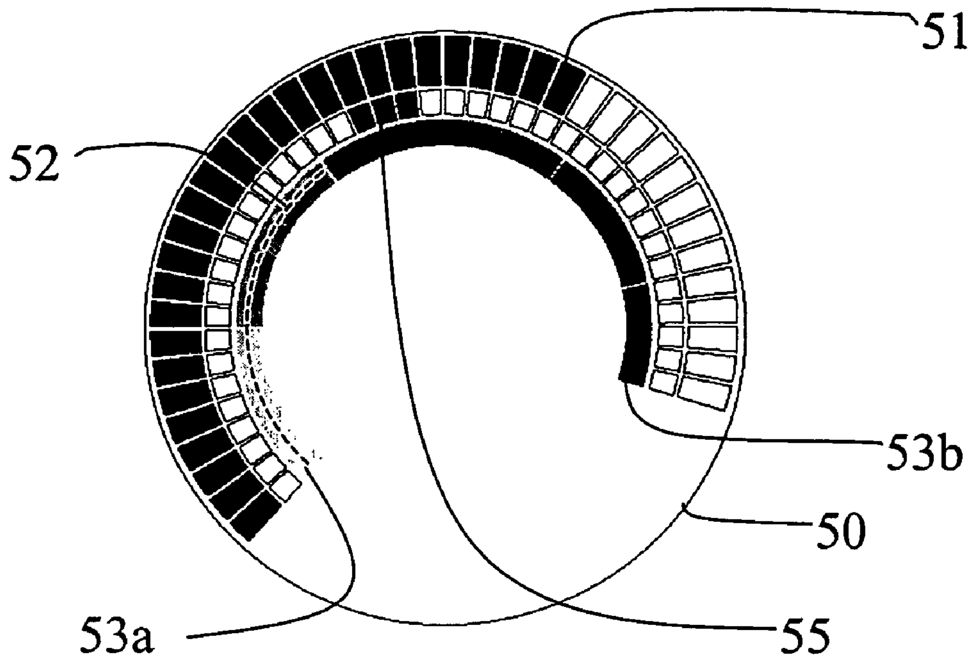
FIG. 5 shows a schematic top view of an embodiment of the invention having a digital current heart rate indicator and a constant reference indicator.

FIG. 5 shows an embodiment, where the heart rate scale is not shown explicitly in numbers. The reference indicator comprises a subrange-indicating arched or sector-type (or equivalent) zone 52 on the dial. The zone is preferably statically attached to the dial, for example, by painting, printing, coating, pasting, gluing or engraving. The training areas can be indicated, for example, by colors. In this case, the lower limit marker 53*a* and the higher limit marker 53*b* correspond to the ends of the zone 52. The current heart rate indicator is located on an orbicular zone within, on top of, or outside the reference indicator. The current heart rate indicator 51 is adapted to take position within the reference zone by adjusting the heart rate scale represented by the current heart rate indicator 51. That is, the dynamic heart rate range the device can output during an exercise may be adjusted to correspond, for example, heart rates between 0 and 220, 50 and 220, 60 and 180, 140 and 170, or anything in between.

The choice of the heart rate scale discussed above can be made by the user or by the device itself. In a preferred embodiment, the scale is adjusted by using heart rate data collected during previous exercises. There may, for example, be defined a calibration program, during which the user has to perform certain tasks and the device monitors the heart rates, decides a heart rate range suitable for the user and adjusts the heart rate scale in relation to (fits the heart rate scale to) the shown reference range. In addition, the scale can depend on a chosen training mode, such as "walking mode", "fat burning mode" or "hard training mode".

An additional display portion 55 can be arranged on the dial for indicating, for example, average of maximum heart rate, duration of training or other functions typically incorporated in heart rate monitors.

The functions of the wristop computer and the indicators can be controlled by using control means, which can comprise, for example, crowns, buttons, or slide switches attached to the body or dial of the device. In analogue embodiments, the control means can be mechanically connected to the indicators for adjusting them. However, in such embodiments, also electro-mechanical implementations, for example, step motors can be used for moving the indicators. In digital embodiments, the control means are preferably connected to a central unit of the device for communicating the commands to a digital display unit. However, the setting of the reference range on the display unit can be also done totally independently of the other functions of the device, because the information of the reference range does not necessarily need to be transmitted to the central unit.

According to an advantageous embodiment, the control means comprises a crown (denoted with a numeral 16, 26 and 36 in FIGS. 1-3). Rotational movement of the crown is easily mechanically transmittable to movement of the reference indicator. In the case of independently-working lower and higher limit markers, (e.g., hands, knobs) the crown can take, for example, two different longitudinal positions for adjusting both the markers separately. Alternatively, rotation of the crown can be converted to electrical signal and the movement of the indicator can be electronically controlled. The position of the indicator may, but does not need to be, in the attention of the device.

Figure 6:
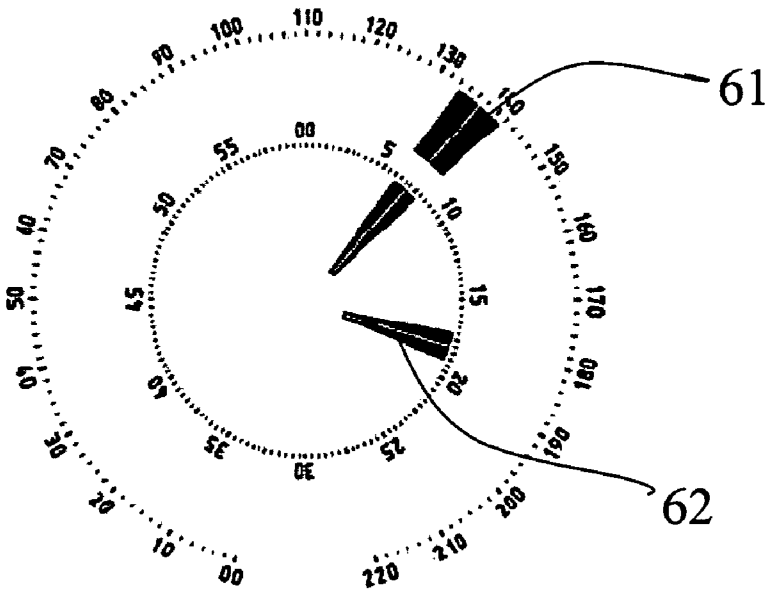
FIG. 6 shows a schematic top view of a second use of digital indicators.

FIG. 6 shows an exemplary use of concentric first and second digital panels as an analogue-type watch. The minute-hand 61 is represented by utilizing both panel area and the hour-hand 62 by the inner panel only. Similar function can be also realized by using other embodiments (analogue and analogue/digital) of the device discussed above. As appreciated by a person skilled in the art, also other features typically housed by wristop computers, such as barometers, altimeters and compasses can be visualized by using the indicators disclosed in this document.

As appreciated by a person skilled in the art, the embodiments disclosed above can be varied and combined within the scope of the invention. In particular, the visual and mechanical representation and implementation of the dial and the indicators can be varied broadly within the scope of the following claims.

The invention claimed is:

1. A method for monitoring a heart rate of a person using a wristop heart rate monitor having a dial, the method comprising indicating current heart rate of the person with a first element rotatably adjustable with respect to the dial and responsive to a heart rate signal measured from the person, and indicating a reference heart rate range by at least one second element, which is statically anchored to the dial, wherein indicating current heart rate is performed by using a heart rate scale, the heart rate scale not being shown explicitly in numbers, and the heart rate scale being adjustable relative to the reference heart rate range.

2. A method according to claim 1, wherein indicating current heart rate is performed by highlighting segments of an electronic display, the display segments being arranged circumferentially and being highlightable one by one.

3. A method according to claim 1, wherein the heart rate scale is fitted to the reference heart rate range by using premeasured data on the physical properties of the person.

4. A method according to claim 1, wherein the heart rate scale is adjusted relative to the reference heart rate range by means of software included in the heart rate monitor.

5. A wristop heart rate monitor having a dial, the dial comprising a current heart rate indicator, which is rotatably adjustable with respect to the dial, responsive to a heart rate signal measured from a user of the wristop computer, and functionally connected to a heart rate scale, where the heart rate scale is not shown explicitly in numbers, and a reference indicator, which is statically anchored to the dial, and defines a visually identifiable reference heart rate range,, wherein the heart rate scale is adjustable relative to the reference heart rate range.

6. A wristop heart rate monitor according to claim 5, which comprises memory for storing heart rate data.

7. A wristop heart rate monitor according to claim 6, which comprises a communications interface for connecting the wristop heart rate monitor to a host device in order to transfer heart rate data to the host device.

8. A wristop heart rate monitor according to claim 5, wherein the indicators are positioned at least partly within each other on the fringe area of the dial.

9. A wristop heart rate monitor according to claim 5, wherein the reference indicator comprises an arc- or disc-shaped member having visually identifiable markers for a plurality of physical training areas.

10. A wristop heart rate monitor according to claim 5, wherein at least one of the indicators comprises a display portion having a plurality of display segments essentially radially arranged with respect to the dial, the display segments being highlightable one by one.

11. A wristop heart rate monitor according to claim 5, which comprises a first elliptical zone and a second elliptical zone, the zones being located within each other on the dial such that the first zone comprises the current heart rate indicator and the second zone comprises the reference indicator.

12. A wristop heart rate monitor according to claim 5, which comprises a communications interface for connecting the heart rate monitor to a host device in order to transfer data on the reference heart rate range to the heart rate monitor.

13. A wristop heart rate monitor according to claim 5, wherein the reference range comprises a lower level marker and a higher level marker and the heart rate scale is adjustable such that the lower level marker points to a lower heart rate and the higher level marker points to a higher heart rate, the lower and higher heart rates being defined using premeasured data on the physical properties of the user of the wristop computer.

14. A wristop heart rate monitor according to claim 5, which comprises a software for adjusting the heart rate scale with respect to the reference heart rate range.

15. A wristop heart rate monitor according to claim 5, which comprises means for fitting the heart rate scale to the reference heart rate range by using premeasured data on the physical properties of the user.

* * * * *